(12) United States Patent
Hölzl et al.

(10) Patent No.: US 8,637,694 B2
(45) Date of Patent: Jan. 28, 2014

(54) ANTIMICROBIAL COMPOUNDS

(75) Inventors: Werner Hölzl, Eschentzwiller (FR); Andrea Preuss, Basel (CH); Michèle Gerster, Binningen (CH)

(73) Assignee: BASF SE, Ludwigshafen (DE)

( * ) Notice: Subject to any disclaimer, the term of this patent is extended or adjusted under 35 U.S.C. 154(b) by 849 days.

(21) Appl. No.: 12/224,006

(22) PCT Filed: Feb. 19, 2007

(86) PCT No.: PCT/EP2007/051548
§ 371 (c)(1),
(2), (4) Date: Dec. 1, 2010

(87) PCT Pub. No.: WO2007/099042
PCT Pub. Date: Sep. 7, 2007

(65) Prior Publication Data
US 2011/0086816 A1    Apr. 14, 2011

(30) Foreign Application Priority Data

Feb. 28, 2006    (EP) .................................... 06110476

(51) Int. Cl.
*A01N 33/12*    (2006.01)
*C08G 77/04*    (2006.01)
*C08G 77/26*    (2006.01)
*C08G 77/388*    (2006.01)

(52) U.S. Cl.
USPC .......................................... 556/425; 556/423

(58) Field of Classification Search
None
See application file for complete search history.

(56) References Cited

U.S. PATENT DOCUMENTS

| | | | |
|---|---|---|---|
| 4,891,166 A | 1/1990 | Schäfer et al. | 554/39 |
| 5,300,167 A | 4/1994 | Nohr et al. | 156/167 |
| 5,569,732 A | 10/1996 | Nohr et al. | 528/27 |
| 6,043,362 A | 3/2000 | Dauth et al. | 544/215 |
| 7,078,550 B2 | 7/2006 | Hölzl et al. | 556/449 |
| 2004/0102570 A1 | 5/2004 | Johnson et al. | 524/838 |
| 2007/0231291 A1 | 10/2007 | Huang et al. | 424/878.3 |

FOREIGN PATENT DOCUMENTS

| | | |
|---|---|---|
| EP | 0017121 | 10/1980 |
| GB | 1154766 | 6/1969 |
| WO | 2005/063872 | 7/2005 |

OTHER PUBLICATIONS

Chem. Abstr. 94:122518 for EP 0017121, Oct. 15, 1980.

*Primary Examiner* — Yevegeny Valenrod
(74) *Attorney, Agent, or Firm* — Shiela A. Loggins

(57) ABSTRACT

The invention relates to cationic siloxane derivatives for use especially as fungicides and/or antiadhesives. The cationic siloxane derivatives have the formula (I), wherein R1, R2, R3, R4, $R_4'$, R5 and n are as defined in the description.

10 Claims, No Drawings

ANTIMICROBIAL COMPOUNDS

SUMMARY OF THE INVENTION

The invention relates to the use of certain salt compounds comprising cationic siloxane derivatives as fungicides and biofilm inhibitors, for the corresponding protection of products and/or materials, and to some novel salt compounds of this class.

BACKGROUND OF THE INVENTION

Colonization by microbes on a wide variety of surfaces and in a variety of materials can cause phenomena such as dirty appearance, smell and even serious hygienic and health problems. Thus there is a great interest in the development of hygienic materials and surfaces which provide biocidal activity and are, at least to some extent, easy to clean or even self-cleaning. There are several attempts to achieve such results by incorporating nano-particles, e.g. on the basis of silver or $TiO_2$: Possible fields of use of coatings or additives leading to the desired surface properties are e.g. architecture and construction, textiled, automobiles and other vehicles for land, air and water, heat exchangers, air conditioning circuits, hygiene, medicine and health e.g. in hospitals, surgery or schools, and food packaging or processing. Among others, the incorporation of nanoparticles into organic resins or ceramics, the deposition in plasma vacuum with deposition of nanoparticles and the like into coatings have been suggested.

On the other hand, certain cationic surfactants are in principle known to be useful as means for cleaning and sometimes even disinfecting surfaces of goods, such as industrial products or consumer articles.

In U.S. Pat. No. 5,569,732, bactericidal additives to thermoplastic materials are described that can carry two cationic groups bound to a siloxane moiety.

What is required, though, also in view of the ability of microorganisms to adapt to a variety of adverse circumstances including the development of resistance, are materials/classes of compounds that allow to inhibit fungal growth or even show microbicidal activity against a broad range of microorganisms, e.g. against fungi as well as one or more microorganisms selected from bacteria, yeasts and algae, and/or even have negative influence on the settlement of multicellular organisms, such as algae, mosses or ferns, on and/or in materials or objects and thus are useful inter alia for applications in preservation, as additives in plastics, in coatings, on textiles, in paper, in cosmetics, in pharmaceutical formulations or corresponding containers, in home or personal care applications and the like, be it with natural and/or with synthetic materials, and for other corresponding uses.

GENERAL DESCRIPTION OF THE INVENTION

It has been found that certain siloxanes substituted with two quaternary ammonium groups surprisingly show good antifungal action.

DETAILED DESCRIPTION OF THE INVENTION

The present invention therefore relates to the use of salt compounds comprising a cation of the formula I,

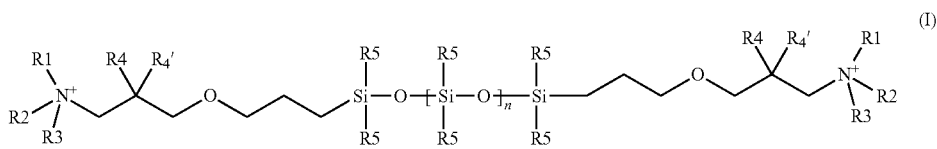

wherein
each of R1, R2 and R3, independently of the others, is $C_1$-$C_{30}$-alkyl, $C_6$-$C_{14}$-aryl-$C_1$-$C_{30}$-alkyl or $C_3$-$C_{10}$-cycloalkyl-$C_1$-$C_{30}$-alkyl, wherein aryl or cycloalkyl is unsubstituted or substituted;
each R4 is, independently of the other, $C_1$-$C_{30}$-alkyl, unsubstituted or substituted $C_3$-$C_{10}$-cycloalkyl, unsubstituted or substituted $C_6$-$C_{14}$-aryl, hydroxy, $C_1$-$C_{30}$-alkoxy, unsubstituted or substituted $C_3$-$C_{30}$-cycloalkoxy, unsubstituted or substituted $C_6$-$C_{30}$-aryloxy, $C_1$-$C_{30}$-alkanoyloxy, unsubstituted or substituted $C_3$-$C_{10}$-cycloalkyl-$C_1$-$C_{30}$-alkanoyloxy, unsubstituted or substituted $C_6$-$C_{14}$-aryl-$C_1$-$C_{30}$-alkanoyloxy, unsubstituted or substituted $C_3$-$C_{10}$-cycloalkylcarbonyloxy or unsubstituted or substituted $C_6$-$C_{14}$-aroyloxy,
and $R_4'$ is hydrogen,
or R4 and $R_4'$ together are oxo;
R5 is, independently of the other, $C_1$-$C_7$-alkyl; and
n is 1 to about 50;
and one or more anions to form a neutral salt,
as a fungicide.

The invention further relates to compositions comprising one or more cations of the formula I which are appropriate especially for covering materials, for addition to materials or products, e.g. by being admixed to materials during their manufacture, and/or for impregnating materials or products, where said compositions may consist of a salt compound of the invention (which expression is used hereinafter to describe a salt compound with a cation of the formula I and appropriate anions as counter-ions) and may in addition comprise other additives, such as binders.

In a further embodiment, the invention relates to the use of one or more salt compounds or compositions according to the invention as defined above or preferably below for the protection of one or more products and/or materials, said use especially comprising adding one or more of said salts or a composition comprising one or more of said salts to said product (article) and/or material, especially for use as fungicide. The addition may be by integration into the material (e.g. by admixing during manufacture of a product, such as an article or a material), by impregnation of an article or material and/or by application to a surface e.g. of an article or material.

Yet a further embodiment relates to a process of manufacture of one or more of the salt compounds of the invention, and/or to a process of manufacture of a composition comprising one or more salts used according to the invention.

The salts according to the invention can be prepared by methods analogous to methods that per se are known in the prior art, though not for the present compounds so that the processes with regard to the salts of the inventions are novel and part of the invention, namely by
a) for the manufacture of a salt compound according to the invention wherein in the cation of the formula I R4 is hydroxy, $C_1$-$C_{30}$-alkoxy, unsubstituted or substituted $C_3$-$C_{30}$-cycloalkoxy, unsubstituted or substituted $C_6$-$C_{30}$-aryloxy, $C_1$-$C_{30}$-alkanoyloxy, unsubstituted or substituted $C_3$-$C_{10}$-cycloalkyl-$C_1$-$C_{30}$-alkanoyloxy, unsubstituted or substituted $C_6$-$C_{14}$-aryl-$C_1$-$C_{30}$-alkanoyloxy, unsubstituted or substituted $C_3$-$C_{10}$-cycloalkylcarbonyloxy or unsubstituted or substituted $C_6$-$C_{14}$-aroyloxy, $R_4'$ is hydrogen and R1, R2, R3, R5 and n are as defined for a cation of the formula I, reacting an epoxide compound of the formula II,

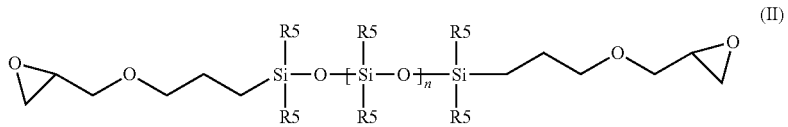

with a tertiary amine of the formula III,

or preferably a salt thereof, wherein R1, R2 and R3 are as defined for a cation of the formula I, to give a corresponding salt compound comprising a cation of the formula I, or b) for the manufacture of a salt compound according to the invention wherein in the cation of the formula I R4 is $C_1$-$C_{30}$-alkyl, unsubstituted or substituted $C_3$-$C_{10}$-cycloalkyl, unsubstituted or substituted $C_6$-$C_{14}$-aryl, and $R_4'$ is hydrogen, or wherein R4 and $R_4'$ together are oxo, reacting a compound of the formula IV,

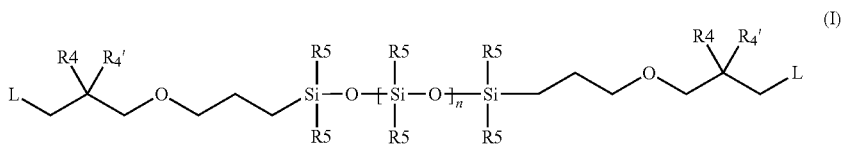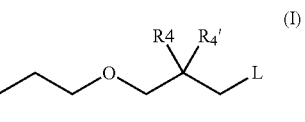

wherein L is a leaving group, R4 is $C_1$-$C_{30}$-alkyl, unsubstituted or substituted $C_3$-$C_{10}$-cycloalkyl, unsubstituted or substituted $C_6$-$C_{14}$-aryl, and $R_4'$ is hydrogen, or wherein R4 and $R_4'$ together are oxo, and wherein R5 and n are as defined for a cation of the formula I, with a compound of the formula III as defined under a), or a salt thereof, to give a corresponding salt compound comprising a cation of the formula I;

and, if desired, a cation of the formula I in a salt obtainable according to a process according to a) and/or b) with a cation of the formula I is subjected to conversion into a different cation of the formula I, and/or a salt obtainable according to a process according to a) and/or b) and/or after conversion with a cation of the formula I is converted into a different salt.

In process variant (a), the reaction preferably takes place under conditions known in the art, for example in an appropriate solvent, such as In process variant b), the quaternization preferably takes place in an appropriate solvent, such as an alcohol, e.g. ethanol, a nitrile, such as acetonitrile, mixtures thereof, or the like, at temperatures, for example, in the range from 0 to 50° C. or at other appropriate temperatures. The leaving group L is preferably halogeno, such as chloro, bromo or iodo, or unsubstituted or substituted phenylsulfonyloxy, such a p-toluolsulfonyloxy.

Among the possible conversions, the conversion of a cation of the formula I wherein R4 is hydroxyl and $R_4'$ is hydrogen to the corresponding cation wherein R4 and $R_4'$ together form oxo by oxidation may be mentioned as example; such oxidation can be carried out according to methods that are known in the art, e.g. by oxidation with $CrO_3$ or other appropriate oxidants in an appropriate solvent or solvent mixture, e.g. water and tetrahydrofuran at temperatures e.g. in the range from 0 to 50° C.

Compound salts of the invention can be converted into different salts by replacing the anions therein by different anions according to customary methods, e.g. by precipitation in the presence of corresponding acids with the desired anions or by using anion exchangers.

The general terms used hereinbefore and hereinafter preferably have within the context of this disclosure the following meanings/definitions, unless otherwise indicated:

$C_1$-$C_{30}$-alkyl can be linear or branched one or more times. It is preferably $C_1$-$C_{20}$-alkyl.

$C_6$-$C_{14}$-aryl is a mono-, bi- or tricyclic aryl moiety with the given number of carbon ring atoms, preferably substituted or more preferably unsubstituted phenyl, naphthyl or fluorenyl. In $C_6$-$C_{14}$-aryl-$C_1$-$C_{30}$-alkyl, the aryl moiety can be bound to any carbon of the alkyl chain; preferably, aryl is bound to the terminal C-atom of $C_1$-$C_{30}$-alkyl. It is preferably substituted or more preferably unsubstituted benzyl.

$C_3$-$C_{10}$-cycloalkyl is preferably a saturated ring with the given range for the number of ring carbon atoms, such as cyclopropyl, cyclobutyl, cyclopentyl or cyclohexyl. In $C_3$-$C_{10}$-cycloalkyl-$C_1$-$C_{30}$-alkyl, the cycloalkyl moiety can be bound to any carbon of the alkyl chain; preferably, cycloalkyl is bound to the terminal C-atom of $A_1$-$C_{30}$-alkyl.

Where a moiety, such as aryl, cycloalkyl or phenyl, is defined as substituted, this means that one or more substitutents, e.g. up to three substituents, preferably independently selected from the group consisting of $C_1$-$C_{20}$-alkyl (more preferably $C_1$-$C_7$-alkyl), phenyl, naphthyl, hydroxy, $C_1$-$C_{20}$-alkoxy, phenyl-, naphthyl-, phenyl-$C_1$-$C_{10}$-alkyl- or naphthyl-$C_1$-$C_{10}$-alkyl-oxy, $C_1$-$C_{20}$-alkanoyloxy, halo, such as fluoro, chloro, bromo or iodo, $C_1$-$C_{20}$-alkoxycarbonyl ($C_1$-$C_{20}$-alkyl-O—C(=O)—), phenoxycarbonyl, naphthoxycarbonyl, phenyl- or naphthyl-$C_1$-$C_{10}$-alkoxycarbonyl, benzoyl, naphthoyl, phenyl- or naphthyl-$C_1$-$C_{10}$-alkanoyl, amino, mono- or di-(phenyl-, naphthyl-, phenyl-$C_1$-$C_{10}$-alkyl- and/or naphthyl-$C_1$-$C_{10}$-alkyl)-amino, nitro and cyano is present.

In $C_1$-$C_{30}$-alkoxy, $C_1$-$C_{30}$-alkyl is preferably as defined above.

In $C_3$-$C_{30}$-cycloalkoxy, $C_3$-$C_{30}$-cycloalkyl is preferably as defined above.

$C_1$-$C_{30}$-alkanoyl is preferably an alkanoyl moiety with the given range for the number of chain atoms and can be linear or branched. Examples are formyl or especially acetyl.

In $C_3$-$C_{10}$-cycloalkyl-$C_1$-$C_{30}$-alkanoyl, the $C_3$-$C_{10}$-cycloalkyl moiety can preferably be bound at the end of the $C_1$-$C_{30}$-alkanoyl moiety, but may also be bound at any different of the carbon atoms of the alkanoyl.

In $C_6$-$C_{14}$-aryl-$C_1$-$C_{30}$-alkanoyl, the $C_6$-$C_{14}$-aryl moiety can preferably be bound at the end of the $C_1$-$C_{30}$-alkanoyl moiety, but may also be bound at any different of the carbon atoms of the alkanoyl.

$C_3$-$C_{10}$-cycloalkylcarbonyloxy is $C_3$-$C_{10}$-cycloalkyl-C(=O)—O—.

$C_6$-$C_{14}$-Aroyloxy is preferably benzoyloxy or naphthoyloxy.

$C_1$-$C_7$-Alkyl is preferably methyl, ethyl, n- or isopropyl, n-, sec- or tert-butyl.

Where in the present disclosure a salt compound comprising or consisting of a cation of the formula I or a cation of the formula I is mentioned, this is intended to include the case where more than one such cation (=type of cation) is present due to different integers for the symbol n falling under the respective "compound" of formula I—in fact, usually mixtures of more than one such cation are present with more than one integer for n, so that in fact usually "a cation of the formula I" is in fact a mixture of cations that fall under the corresponding formula (in the case of the Examples, formula Ia, Ib, Ic, Id, Ie and If (which all fall under formula I) this definition is also to be applied), thus meaning that "a salt compound" is in fact a mixture of salt compounds. Therefore, "a salt compound" also includes more than one such salt compound, that is, a compound mixture falling under the corresponding definition. The same is also true for precursors and starting materials, e.g. of the formula II or IV. Where one or more anions are mentioned, this refers to one type or more than one type of anions present (e.g. mixtures of anions or one pure type of anions). Where the plural ("Salt compounds", "cations", "anions", "precursors", starting materials" or the like) form is used, this also includes one compound, cation, anion, precursor, starting material or the like, respectively.

An anion or anions to form a neutral salt of a cation of the formula I means preferably that in a salt according to the invention per cation of the formula I, per cation of the formula I p anions of the formula (IA)

$$Y^{(3-p)-} \quad (IA)$$

are present (with different of preferably identical Y) wherein Y is an anion molecule with the integer number of negative charges determined by (3-p) and p is 1 or 2. However, it is also possible that anions with three- or higher-fold negative charge are employed, such as phosphate or polyphosphates, thus leading to salts where less than one anion is present per cation of the formula I. Preferred examples are halogenide, such as chloride, iodide, bromide or fluoride, sulfate, hydrogensulfate, nitrate, hydrogenphosphate, phosphate, borate, tetrafluoroborate, acetate, citrate, p-toluenesulfate, methansulfonate (MeSO$_3^-$), methyloxysulfonate (MeO—SO$_3^-$), trifluoromethansulfonate, nonafluorobutanesulfonate, 2,2,2-trifluoromethanesulfonate, fluorosulfonate or the like. In all cases, the stoichiometry of the anions and cations is such that a neutral salt according to the invention is formed.

A preferred molecular weight of a cation of the formula I is in the range from about 600 to about 3000.

A preferred polydispersity (ration of the weight average to the number average molecular weight) of said cations is in the range of up to about 3.

"About" wherever used in the present disclosure means that a certain deviation from a numerical value may be present and the corresponding value is not intended to mean an absolute boarder as will be apparent to a person skilled in the art; it preferably means "±20%" of the respective numerical value, more preferably "±10%", yet more preferably "±5%" thereof, and most preferably can be deleted so that only the respective numerical value remains without preceding "about".

Integration, admixing, impregnation, impregnating and/or coating includes homogenous integration or admixing, in homogenous integration or admixing, complete or partial impregnation and/or complete or partial coating.

Compositions for use according to the invention, which are also called anti-fouling compositions (or which can also be called antimicrobial or especially antifungal compositions) hereinafter, may, in addition to salt compound of formula I which may also be present as sole component of the composition, comprise other additives such as a binder, solvents or the like. The invention also comprises the antifungal and combined antifungal/antibacterial use of a salt compound of formula I or such a composition.

The binder may be any polymer or oligomer compatible with the present. The binder may be in the form of a polymer or oligomer prior to preparation of the anti-fouling composition, or may form by polymerization during or after preparation, including after application to the substrate.

The term binder as used in the present invention also includes materials such as glycols, oils, waxes and surfactants commercially used in the care of wood, plastic, glass and other surfaces. Examples include water proofing materials for wood, vinyl protectants, protective waxes and the like.

The antifouling composition of the invention may be a coating or a film, a composition for admixing to a material and/or a composition for impregnating a material and/or a product. When the antifouling composition is a thermoplastic film which is applied to a surface, for example, by the use of an adhesive or by melt applications including calendaring and co-extrusion, the binder is the thermoplastic polymer matrix used to prepare the film.

When the antifouling composition is, e.g., a coating, it may be applied as a liquid solution or suspension, a paste, gel, oil or the coating composition may be a solid, for example a powder coating which is subsequently cured by heat, UV light or other method. As the antifouling composition of the invention may be a coating or a film, the binder can be comprised of any polymer used in coating formulations or film preparation.

For example, the binder is a thermoset, thermoplastic, elastomeric, inherently crosslinked or crosslinked polymer. Thermoset, thermoplastic, elastomeric, inherently crosslinked or crosslinked polymers include polyolefin, polyamide, polyurethane, polyacrylate, polyacrylamide, polycarbonate, polystyrene, polyvinyl acetates, polyvinyl alcohols, polyester, halogenated vinyl polymers such as PVC, natural and synthetic rubbers, alkyd resins, epoxy resins, unsaturated polyesters, unsaturated polyamides, polyimides, silicon containing and carbamate polymers, fluorinated polymers, crosslinkable acrylic resins derived from substituted acrylic esters, e.g. from epoxy acrylates, urethane acrylates or polyester acrylates. The polymers may also be blends and copolymers of the preceding chemistries.

Examples of thermoplastic, elastomeric, inherently crosslinked or crosslinked polymers are listed below.

1. Polymers of mono- and di-olefins, for example polypropylene, polyisobutylene, polybutene-1, poly-4-methylpentene-1, polyisoprene or polybutadiene and also polymerisates of cyclo-olefins, for example of cyclopentene or norbornene; and also polyethylene (which may optionally be crosslinked), for example high density polyethylene (HDPE), high density polyethylene of high molecular weight (HDPE-HMW), high density polyethylene of ultra-high molecular weight (HDPE-UHMW), medium density polyethylene (MDPE), low density polyethylene (LDPE), and linear low density polyethylene (LLDPE), (VLDPE) and (ULDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of mono- and di-olefins with one another or with other vinyl monomers, for example ethylene/propylene copolymers, linear low density polyethylene (LLDPE) and mixtures thereof with low density polyethylene (LDPE), propylene/butene-1 copolymers, propylene/isobutylene copolymers, ethylene/butene-1 copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/-alkyl acrylate copolymers, ethylene/alkyl methacrylate copolymers, ethylene/vinyl acetate copolymers and copolymers thereof with carbon monoxide, or ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another or with polymers mentioned under 1), for example polypropylene-ethylene/propylene copolymers, LDPE-ethylene/vinyl acetate copolymers, LDPE-ethylene/acrylic acid copolymers, LLDPE-ethylene/vinyl acetate copolymers, LLDPE-ethylene/acrylic acid copolymers and alternately or randomly structured polyalkylene-carbon monoxide copolymers and mixtures thereof with other polymers, for example polyamides.

4. Hydrocarbon resins (for example $C_5$-$C_9$) including hydrogenated modifications thereof (for example tackifier resins) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate and methacrylate, styrene/maleic anhydride, styrene/acrylonitrile/methyl acrylate; high-impact-strength mixtures consisting of styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene/ethylene-propylene/-styrene.

7. Graft copolymers of styrene or α-methylstyrene, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleic acid imide on polybutadiene; styrene and maleic acid imide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under 6), such as those known, for example, as so-called ABS, MBS, ASA or AES polymers.

8. Halogen-containing polymers, for example polychloroprene, chlorinated rubber, chlorinated and brominated copolymer of isobutylene/isoprene (halobutyl rubber), chlorinated or chlorosulfonated polyethylene, copolymers of ethylene and chlorinated ethylene, epichlorohydrin homo- and co-polymers, especially polymers of halogen-containing vinyl compounds, for example polyvinyl chloride, polyvinylidene chloride, polyvinyl fluoride, polyvinylidene fluoride; and copolymers thereof, such as vinyl chloride/vinylidene chloride, vinyl chloride/vinyl acetate or vinylidene chloride/vinyl acetate.

9. Polymers derived from α,β-unsaturated acids and derivatives thereof, such as polyacrylates and polymethacrylates, or polymethyl methacrylates, polyacrylamides and polyacrylonitriles impact-resistant-modified with butyl acrylate.

10. Copolymers of the monomers mentioned under 9) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

11. Polymers derived from unsaturated alcohols and amines or their acyl derivatives or acetals, such as polyvinyl alcohol, polyvinyl acetate, stearate, benzoate or maleate, polyvinylbutyral, polyalkyl phthalate, polyallylmelamine; and the copolymers thereof with olefins mentioned in Point 1.

12. Homo- and co-polymers of cyclic ethers, such as polyalkylene glycols, polyethylene oxide, polypropylene oxide or copolymers thereof with bisglycidyl ethers.

13. Polyacetals, such as polyoxymethylene, and also those polyoxyethylenes which contain comonomers, for example ethylene oxide; polyacetals modified with thermoplastic polyurethanes, acrylates or MBS.

14. Polyphenylene oxides and sulfides and mixtures thereof with styrene polymers or polyamides.

15. Polyurethanes derived from polyethers, polyesters and polybutadienes having terminal hydroxyl groups on the one hand and aliphatic or aromatic polyisocyanates on the other hand, and their initial products.

16. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides derived from m-xylene, diamine and adipic acid; polyamides prepared from hexamethylenediamine and iso- and/or tere-phthalic acid and optionally an elastomer as modifier, for example poly-2,4,4-trimethylhexamethylene terephthalamide or poly-m-phenylene isophthalamide. Block copolymers of the above-mentioned polyamides with polyolefins, olefin copolymers, ionomers or chemically bonded or grafted elastomers; or with polyethers, for example with polyethylene glycol, polypropylene glycol or polytetramethylene glycol. Also polyamides or copolyamides modified with EPDM or ABS; and polyamides condensed during processing ("RIM polyamide systems").

17. Polyureas, polyimides, polyamide imides, polyether imides, polyester imides, polyhydantoins and polybenzimidazoles.

18. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, and also block polyether esters derived from polyethers with hydroxyl terminal groups; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, urea or melamine on the other hand, such as phenol-formaldehyde, urea-formaldehyde and melamine-formaldehyde resins.

22. Drying and non-drying alkyd resins.
23. Unsaturated polyester resins derived from copolyesters of saturated and unsaturated dicarboxylic acids with polyhydric alcohols, and also vinyl compounds as crosslinking agents, and also the halogen-containing, difficulty combustible modifications thereof.
24. Crosslinkable acrylic resins derived from substituted acrylic esters, e.g. from epoxy acrylates, urethane acrylates or polyester acrylates.
25. Alkyd resins, polyester resins and acrylate resins that are crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, e.g. products of bisphenol-A diglycidyl ethers, bisphenol-F diglycidyl ethers, that are crosslinked using customary hardeners, e.g. anhydrides or amines with or without accelerators.
27. Mixtures (polyblends) of the afore-mentioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Acrylic, methacrylic and acrylamide polymers and co-polymers dispersible in water are readily used as a binder in the present invention. For example, acrylic, methacrylic and acrylamide dispersion polymers and co-polymers are used as binders in the anti-fouling coatings.

Biocompatible coating polymers, such as, poly[-alkoxyalkanoate-co-3-hydroxyalkenoate] (PHAE) polyesters, Geiger et. al. Polymer Bulletin 52, 65-70 (2004), can also serve as binders in the present invention.

Alkyd resins, polyesters, polyurethanes, epoxy resins, silicone containing polymers, fluorinated polymers and polymers of vinyl acetate, vinyl alcohol and vinyl amine are non-limiting examples of common coating binders useful in the present invention. Other coating binders, of course, are part of the present invention.

Coatings are frequently crosslinked with, for example, melamine resins, urea resins, isocyanates, isocyanurates, polyisocyanates, epoxy resins, anhydrides, poly acids and/or amines, with or without accelerators.

The anti-fouling compositions of present invention are for example used as a coating applied to a surface which is exposed to conditions favorable for bioaccumulation. The presence of the cations of formula I in said coating will prevent the adherence of organisms, especially fungi, to the surface.

The anti-fouling composition of the present invention may be part of a complete coating or paint formulation, such as a marine gel-coat, shellac, varnish, lacquer or paint, or the anti fouling composition may comprise only a compound of formula I and binder, or a compound of formula I, binder and one or more additives. It is anticipated that other additives encountered in such coating formulations or applications will find optional use in the present applications as well.

The composition, e.g. coating, may be solvent borne or aqueous. Aqueous compositions are typically considered more environmentally friendly.

The coating or other composition according to the invention is, for example, aqueous dispersion of a salt compound according to the invention and a binder or a water based coating or paint. For example, the coating comprises an aqueous dispersion of a salt compound with a cation of formula I and acrylic, methacrylic or acrylamide polymers or co-polymers or a poly[-alkoxyalkanoate-co-3-hydroxyalkenoate] polyester.

The coating is, for example, a coating or varnish used in marine applications. Such a coating may be applied to a surface which has already been coated, such as a protective coating, a clear coat or a protective wax applied on top of a previously coated article, and/or or it may be used to impregnate a material or product.

Coating systems include marine coatings, wood coatings, other coatings for metals and coatings over plastics and ceramics. Exemplary of marine coatings are gel coats comprising an unsaturated polyester, a styrene and a catalyst.

The coating is, for example a house paint, or other decorative or protective paint. It may be a paint or other coating that is applied to cement, concrete or other masonry article. The coating may be a water proofer as for a basement or foundation.

As the anti-fouling composition is intended for use in maritime applications as well as near pool areas etc., the composition may be part of a non-skid coating including coatings for stairs, paths and handrails.

The coating composition is applied to a surface by any conventional means including spin coating, dip coating, spray coating, draw down, or by brush, roller or other applicator. A drying or curing period will typically be needed. For impregnating, it is also possible to use pressure impregnation or impregnation without pressure application.

Coating or film thickness will vary depending on application and will become apparent to one skilled in the art after limited testing.

The anti-fouling composition may be applied in the form of a protective laminate film. Such a film typically comprises thermoset, thermoplastic, elastomeric, or crosslinked polymers. Examples of such polymers include, but are not limited to, polyolefin, polyamide, polyurethane, polyacrylate, polyacrylamide, polycarbonate, polystyrene, polyvinyl acetates, polyvinyl alcohols, polyester, halogenated vinyl polymers such as PVC, natural and synthetic rubbers, alkyd resins, epoxy resins, unsaturated polyesters, unsaturated polyamides, polyimides, fluorinated polymers, silicon containing (other than of formula I) and carbamate polymers. The polymers may also be blends and copolymers of the preceeding chemistries.

When the anti-fouling composition is a preformed film it is applied to the surface by, for example, the use of an adhesive, or co-extruded onto the surface. It may also be mechanically affixed via fasteners which may require the use of a sealant or caulk wherein the esters of the instant invention may also be advantageously employed.

A plastic film may also be applied with heat which includes calendaring, melt applications and shrink wrapping.

The anti-fouling composition may be part of a polish, such a furniture polish, or a dispersant or surfactant formulation such as a glycol or mineral oil dispersion or other formulation as used in for example wood protection, paper or cardboard protection or the like.

Examples of useful surfactants include, but are not limited to, polyoxyethylene-based surface-active substances, including polyoxyethylene sorbitan tetraoleate (PST), polyoxyethylene sorbitol hexaoleate (PSH), polyoxyethylene 6 tridecyl ether, polyoxyethylene 12 tridecyl ether, polyoxyethylene 18 tridecyl ether, Tween® surfactants, Triton® surfactants, and the polyoxyethlene-polyoxypropylene copolymers such as the Pluronic® and Poloxamer® product series (from BASF). Other matrix-forming components include dextrans, linear PEG molecules (MW 500 to 5,000,000), star-shaped PEG molecules, comb-shaped and dendrimeric, hyperbranched PEG molecules, as well as the analogous linear, star, and dendrimer polyamine polymers, and various carbonated, perfluorinated (e.g., DuPont Zonyl® fluorosurfactants) and siliconated (e.g., dimethylsiloxane-ethylene oxide block copolymers) surfactants (other than those of the present invention).

Given the wide array of applications for the present antifouling compositions, the composition may contain one or more other additives such as antioxidants, UV absorbers, hindered amines, phosphites or phosphonites, benzofuran-2-ones, thiosynergists, polyamide stabilizers, metal stearates, nucleating agents, fillers, reinforcing agents, lubricants, emulsifiers, dyes, pigments, dispersants, other optical brighteners, flame retardants, antistatic agents, blowing agents and the like, such as the materials listed below, or mixtures thereof.

1. Antioxidants
1.1. Alkylated Phenols
for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1-methylundec-1-yl)phenol, 2,4-dimethyl-6-(1-methylheptadec-1-yl)phenol, 2,4-dimethyl-6-(1-methyltridec-1-yl)phenol, propyl gallate and mixtures thereof.

1.2. Alkylthiomethylphenols
for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and Alkylated Hydroquinones
for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols
for example α-tocopherol, β-tocopherol, γ-tocopherol, δ-tocopherol and mixtures thereof (Vitamin E).

1.5. Hydroxylated Thiodiphenyl Ethers
for example 2, 2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols
for example 2, 2'-methylenebis(6-tert-butyl-4-methylphenol), 2,2'-methylenebis(6-tert-butyl-4-ethylphenol), 2,2'-methylenebis[4-methyl-6-(-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)-butane, 1,1-bis(5-tert-butyl-4-hydroxy-2-methyl-phenyl)-3-n-dodecylmercaptobutane, ethylene glycol bis[3,3-bis(3-tert-butyl-4-hydroxyphenyl)butyrate], bis(3-tert-butyl-4-hydroxy-5-methyl-phenyl)dicyclopentadiene, bis[2-(3'tert-butyl-2-hydroxy-5-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. Benzyl Compounds
for example 3, 5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, 1,3,5-tri-(3,5-di-tert-butyl-4-hydroxybenzyl)-2,4,6-trimethylbenzene, di-(3,5-di-tert-butyl-4-hydroxybenzyl) sulfide, 3,5-di-tert-butyl-4-hydroxybenzyl-mercapto-acetic acid isooctyl ester, bis-(4-tert-butyl-3-hydroxy-2,6-dimethylbenzyl)dithiol terephthalate, 1,3,5-tris-(3,5-di-tert-butyl-4-hydroxybenzyl)isocyanurate, 1,3,5-tris-(4-tert-butyl-3-hydroxy-2,6-dimethylbenzyl)isocyanurate, 3,5-di-tert-butyl-4-hydroxybenzyl-phosphoric acid dioctadecyl ester and 3,5-di-tert-butyl-4-hydroxybenzyl-phosphoric acid monoethyl ester, calcium-salt.

1.8. Hydroxybenzylated Malonates
for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic Hydroxybenzyl Compounds
for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds
for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl) isocyanurate, 1,3,5-tris(4-tert-butyl-3-hydroxy-2,6-dimethylbenzyl)-isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates
for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols
for example 4-hydroxy-lauric acid anilide, 4-hydroxystearic acid anilide, 2,4-bis-octylmercapto-6-(3,5-di-tert-butyl-4-hydroxyanilino)-s-triazine and octyl-N-(3,5-di-tert-butyl-4-hydroxyphenyl)-carbamate.

1.13. Esters of β-(3,5-di-tert-butyl-4-hydroxyphenyl)propionic acid
with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid
with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl)propionic acid
with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid
with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid
e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)-ethyl]oxamide (Naugard®XL-1 supplied by Uniroyal).

1.18. Ascorbic Acid (Vitamin C)

1.19. Aminic Antioxidants
for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-α-tylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)-biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilizers 2.1. 2-(2-Hydroxyphenyl)-2H-benzotriazoles
for example known commercial hydroxyphenyl-2H-benzotriazoles and benzotriazoles as disclosed in, U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905; 4,853,471; 5,268,450; 5,278,314; 5,280,124; 5,319,091; 5,410,071; 5,436,349; 5,516,914; 5,554,760; 5,563,242; 5,574,166; 5,607,987 and 5,977,219, such as 2-(2-hydroxy-5-methylphenyl)-2H-benzotriazole, 2-(3,5-di-t-butyl-2-hydroxyphenyl)-2H-benzotriazole, 2-(2-hydroxy-5-t-butylphenyl)-2H-benzotriazole, 2-(2-hydroxy-5-t-octylphenyl)-2H-benzotriazole, 5-chloro-2-(3,5-di-t-butyl-2-hydroxyphenyl)-2H-benzotriazole, 5-chloro-2-(3-t-butyl-2-hydroxy-5-methylphenyl)-2H-benzotriazole, 2-(3-secbutyl-5-t-butyl-2-hydroxyphenyl)-2H-benzotriazole, 2-(2-hydroxy-4-octyloxyphenyl)-2H-benzotriazole, 2-(3,5-di-t-amyl-2-hydroxyphenyl)-2H-benzotriazole, 2-(3,5-bis-α-cumyl-2-hydroxyphenyl)-2H-benzotriazole, 2-(3-t-butyl-2-hydroxy-5-(2-(ω-hydroxy-octa-(ethyleneoxy)carbonyl-ethyl), phenyl)-2H-benzotriazole, 2-(3-dodecyl-2-hydroxy-5-methylphenyl)-2H-benzotriazole, 2-(3-t-butyl-2-hydroxy-5-(2-octyloxycarbonyl)ethylphenyl)-2H-benzotriazole, dodecylated 2-(2-hydroxy-5-methylphenyl)-2H-benzotriazole, 2-(3-t-butyl-2-hydroxy-5-(2-octyloxycarbonylethyl)phenyl)-5-chloro-2H-benzotriazole, 2-(3-tert-butyl-5-(2-(2-ethylhexyloxy)-carbonylethyl)-2-hydroxyphenyl)-5-chloro-2H-benzotriazole, 2-(3-t-butyl-2-hydroxy-5-(2-methoxycarbonylethyl)phenyl)-5-chloro-2H-benzotriazole, 2-(3-t-butyl-2-hydroxy-5-(2-methoxycarbonylethyl)phenyl)-2H-benzotriazole, 2-(3-t-butyl-5-(2-(2-ethylhexyloxy)carbonylethyl)-2-hydroxyphenyl)-2H-benzotriazole, 2-(3-t-butyl-2-hydroxy-5-(2-isooctyloxycarbonylethyl)-phenyl-2H-benzotriazole, 2,2'-methylene-bis(4-t-octyl-(6-2H-benzotriazol-2-yl)phenol), 2-(2-hydroxy-3-α-cumyl-5-t-octylphenyl)-2H-benzotriazole, 2-(2-hydroxy-3-t-octyl-5-α-cumylphenyl)-2H-benzotriazole, 5-fluoro-2-(2-hydroxy-3,5-di-α-cumylphenyl)-2H-benzotriazole, 5-chloro-2-(2-hydroxy-3,5-di-α-cumylphenyl)-2H-benzotriazole, 5-chloro-2-(2-hydroxy-3-α-cumyl-5-t-octylphenyl)-2H-benzotriazole, 2-(3-t-butyl-2-hydroxy-5-(2-isooctyloxycarbonylethyl)phenyl)-5-chloro-2H-benzotriazole, 5-trifluoromethyl-2-(2-hydroxy-3-α-cumyl-5-t-octylphenyl)-2H-benzotriazole, 5-trifluoromethyl-2-(2-hydroxy-5-t-octylphenyl)-2H-benzotriazole, 5-trifluoromethyl-2-(2-hydroxy-3,5-di-t-octylphenyl)-2H-benzotriazole, methyl 3-(5-trifluoromethyl-2H-benzotriazol-2-yl)-5-t-butyl-4-hydroxyhydrocinnamate, 5-butylsulfonyl-2-(2-hydroxy-3-α-cumyl-5-t-octylphenyl)-2H-benzotriazole, 5-trifluoromethyl-2-(2-hydroxy-3-α-cumyl-5-t-butylphenyl)-2H-benzotriazole, 5-trifluoromethyl-2-(2-hydroxy-3,5-di-t-butylphenyl)-2H-benzotriazole, 5-trifluoromethyl-2-(2-hydroxy-3,5-di-α-cumylphenyl)-2H-benzotriazole, 5-butylsulfonyl-2-(2-hydroxy-3,5-di-t-butylphenyl)-2H-benzotriazole and 5-phenylsulfonyl-2-(2-hydroxy-3,5-di-t-butylphenyl)-2H-benzotriazole.

2.2. 2-Hydroxybenzophenones
for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of Substituted and Unsubstituted Benzoic Acids
as for example 4-tertbutyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates and Malonates
for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline, Sanduvor® PR25, dimethyl p-methoxybenzylidenemalonate (CAS#7443-25-6), and Sanduvor® PR31, di-(1,2,2,6,6-pentamethylpiperidin-4-yl) p-methoxybenzylidenemalonate (CAS#147783-69-5).

2.5. Nickel Compounds
for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically Hindered Amine Stabilizers
for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis-(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cyclounaecyl-1-oxa-3,8-diaza-4-oxospiro [4,5]decane and epichlorohydrin, 1,1-bis(1,2,2,6,6-pentamethyl-4-piperidyloxycarbonyl)-2-(4-methoxyphenyl) ethene, N,N'-bis-formyl-N,N'-bis(2,2,6,6-tetramethyl-4-piperidyl)hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine. The sterically hindered amine may also be one of the compounds described in GB-A-2301106 as component I-a), I-b), I-c), I-d), I-e), I-f), I-g), I-h), I-i), I-j), I-k) or I-l), in particular the light stabilizer 1-a-1, 1-a-2, 1-b-1, 1-c-1, 1-c-2, 1-d-1, 1-d-2, 1-d-3, 1-e-1, 1-f-1, 1-g-1, 1-g-2 or 1-k-1 listed on pages 68 to 73 of said GB-A-2301106. The sterically hindered amine may also be one of the compounds described in EP 782994, for example compounds as described in claims or in Examples 1-12 or D-1 to D-5 therein. The sterically hindered amine may also be a hydroxylamine, hydroxylamine salt or nitroxl derivatives of hindered amine light stabilizers.

2.7. Sterically Hindered Amines Substituted on the N-Atom by a Hydroxy-Substituted Alkoxy Group
for example compounds such as 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine with a carbon radical from t-amylalcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethylpiperidin-4-yl) sebacate, bis(1-(2-hydroxy-2-methylpropoxy)-2,2,6,6-tetramethylpiperidin-4-yl)adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin-4-yl)glutarate and 2,4-bis{N-[1-(2-hydroxy-2-methylpropoxy)-2,2,6,6-tetramethylpiperidin-4-yl]-N-butylamino}-6-(2-hydroxy-ethylamino)-s-triazine.

2.8. Oxamides
for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of n- and p-methoxy-disubstituted oxanilides and mixtures of o- and p-ethoxy-disubstituted oxanilides.

2.9. Tris-aryl-o-hydroxyphenyl-s-triazines
for example known commercial tris-aryl-o-hydroxyphenyl-s-triazines and triazines as disclosed in, WO 96/28431, EP 434608, EP 941989, GB 2,317,893, U.S. Pat. Nos. 3,843,371; 4,619,956; 4,740,542; 5,096,489; 5,106,891; 5,298,067;

5,300,414; 5,354,794; 5,461,151; 5,476,937; 5,489,503; 5,543,518; 5,556,973; 5,597,854; 5,681,955; 5,726,309; 5,942,626; 5,959,008; 5,998,116 and 6,013,704, for example 4,6-bis-(2,4-dimethylphenyl)-2-(2-hydroxy-4-octyloxyphenyl)-s-triazine, Cyasorb® 1164, Cytec Corp, 4,6-bis-(2,4-dimethylphenyl)-2-(2,4-dihydroxyphenyl)-s-triazine, 2,4-bis(2,4-dihydroxyphenyl)-6-(4-chlorophenyl)-s-triazine, 2,4-bis[2-hydroxy-4-(2-hydroxyethoxy)phenyl]-6-(4-chlorophenyl)-s-triazine, 2,4-bis[2-hydroxy-4-(2-hydroxy-4-(2-hydroxyethoxy)phenyl]-6-(2,4-dimethylphenyl)-s-triazine, 2,4-bis[2-hydroxy-4-(2-hydroxyethoxy)phenyl]-6-(4-bromophenyl)-s-triazine, 2,4-bis[2-hydroxy-4-(2-acetoxyethoxy)phenyl]-6-(4-chlorophenyl)-s-triazine, 2,4-bis(2,4-dihydroxyphenyl)-6-(2,4-di-methylphenyl)-s-triazine, 2,4-bis(4-biphenylyl)-6-(2-hydroxy-4-octyloxycarbonylethylidene-oxyphenyl)-s-triazine, 2-phenyl-4-[2-hydroxy-4-(3-sec-butyloxy-2-hydroxypropyloxy)phenyl]-6-[2-hydroxy-4-(3-sec-amyloxy-2-hydroxypropyloxy)phenyl]-s-triazine, 2,4-bis(2,4-dimethylphenyl)-6-[2-hydroxy-4-(3-benzyloxy-2-hydroxypropyloxy)phenyl]-s-triazine, 2,4-bis(2-hydroxy-4-n-butyloxyphenyl)-6-(2,4-di-n-butyloxyphenyl)-s-triazine, 2,4-bis(2,4-dimethylphenyl)-6-[2-hydroxy-4-(3-nonyloxy*-2-hydroxypropyloxy)-5-α-cumylphenyl]-s-triazine (* denotes a mixture of octyloxy, nonyloxy and decyloxy groups), methylenebis-{2,4-bis(2,4-dimethylphenyl)-6-[2-hydroxy-4-(3-butyloxy-2-hydroxypropoxy)phenyl]-s-triazine}, methylene bridged dimer mixture bridged in the 3:5', 5:5' and 3:3' positions in a 5:4:1 ratio, 2,4,6-tris(2-hydroxy-4-isooctyloxycarbonylisopropylideneoxyphenyl)-s-triazine, 2,4-bis(2,4-dimethylphenyl)-6-(2-hydroxy-4-hexyloxy-5-α-cumylphenyl)-s-triazine, 2-(2,4,6-trimethylphenyl)-4,6-bis[2-hydroxy-4-(3-butyloxy-2-hydroxypropyloxy)phenyl]-s-triazine, 2,4,6-tris[2-hydroxy-4-(3-sec-butyloxy-2-hydroxypropyloxy)phenyl]-s-triazine, mixture of 4,6-bis-(2,4-dimethylphenyl)-2-(2-hydroxy-4-(3-dodecyloxy-2-hydroxypropoxy)-phenyl)-s-triazine and 4,6-bis-(2,4-dimethylphenyl)-2-(2-hydroxy-4-(3-tridecyloxy-2-hydroxypropoxy)-phenyl)-s-triazine, Tinuvin® 400, Ciba Specialty Chemicals Corp., 4,6-bis-(2,4-dimethylphenyl)-2-(2-hydroxy-4-(3-(2-ethylhexyloxy)-2-hydroxypropoxy)-phenyl)-s-triazine and 4,6-diphenyl-2-(4-hexyloxy-2-hydroxyphenyl)-s-triazine.

3. Metal Deactivators for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl) thiopropionyl dihydrazide.

4. Phosphites and Phosphonites for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl)pentaerythritol diphosphite (Ultranox® 626, GE Chemicals, formula (D)), bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butyl-phenyl)pentaerythritol diphosphite, tristearyl sorbitol triphosphite, tetrakis(2,4-di-tert-butyl-phenyl) 4,4'-biphenylene diphosphonite (Irgafos® P-EPQ, Ciba Specialty Chemicals Corp., formula (H)), 6-isooctyloxy-2,4,8,10-tetra-tert-butyl-dibenzo[d,f][1,3,2]dioxaphosphepin, 6-fluoro-2,4,8,10-tetra-tert-butyl-12-methyl-dibenzo[d,g][1,3,2]dioxaphosphocin, bis(2,4-di-tert-butyl-6-methylphenyl)methyl phosphite, bis(2,4-di-tert-butyl-6-methylphenyl)ethyl phosphite, 2,2',2"-nitrilo[triethyltris(3,3',5,5'-tetra-tert-butyl-1,1-biphenyl-2,2'-diyl)phosphite], 2-ethylhexyl(3,3',5,5'-tetra-tert-butyl-1,1'-biphenyl-2,2'-diyl)phosphite.

5. Benzofuranones and Indolinones for example those disclosed in U.S. Pat. Nos. 4,325,863, 4,338,244, 5,175,312, 5,216,052, 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, Irganox® HP-136, Ciba Specialty Chemicals Corp., and 3-(2,3-dimethylphenyl)-5,7-di-tert-butyl-benzofuran-2-one.

6. Hydroxylamines for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N-methyl-N-octadecyl-hydroxylamine and the N,N-dialkylhydroxylamine derived from hydrogenated tallow amine.

7. Nitrones for example N-benzyl-α-phenylnitrone, N-ethyl-α-methylnitrene, N-octyl-α-heptylnitrone, N-lauryl-α-undecylnitrone, N-tetradecyl-α-tridcylnitrone, N-hexadecyl-α-pentadecylnitrone, N-octadecyl-α-heptadecylnitrone, N-hexadecyl-α-heptadecylnitrone, N-ocatadecyl-α-pentadecylnitrone, N-heptadecyl-α-heptadecylnitrone, N-octadecyl-α-hexadecylnitrone, N-methyl-α-heptadecylnitrone and the nitrone derived from N,N-dialkylhydroxyl amine derived from hydrogenated tallow amine.

8. Amine Oxides for example amine oxide derivatives as disclosed in U.S. Pat. Nos. 5,844,029 and 5,880,191, didecyl methyl amine oxide, tridecyl amine oxide, tridodecyl amine oxide and trihexadecyl amine oxide.

9. Thiosynergists for example dilauryl thiodipropionate or distearyl thiodipropionate.

10. Peroxide Scavengers for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

11. Polyamide Stabilizers for example copper salts in combination with iodides and/or phosphorus compounds and salts of divalent manganese.

12. Basic Co-Stabilizers for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium palmitate, antimony pyrocatecholate or zinc pyrocatecholate.

13. Nucleating Agents for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

14. Fillers and Reinforcing Agents for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

15. Dispersing Agents such as polyethylene oxide waxes or mineral oil.

16. Other Additives for example plasticizers, lubricants, emulsifiers, pigments, dyes, other optical brighteners, rheology additives, catalysts, flow-control agents, slip agents, crosslinking agents, crosslinking boosters, halogen scavengers, smoke inhibitors, flame-proofing agents, antistatic agents, clarifiers such as substituted and unsubstituted bisbenzylidene sorbitols, benzoxazinone UV absorbers such as 2,2'-p-phenylene-bis(3,1-benzoxazin-4-one), Cyasorb® 3638 (CAS#18600-59-4), and blowing agents.

The surface being coated or laminated or impregnated is the surface of any substrate (other word for material or product used herein) exposed to biofouling conditions. The substrate can be an inorganic or organic substrate, for example, based on a metal or metal alloy; a thermoplastic, elastomeric, inherently crosslinked or crosslinked polymer as described above; a natural polymer such as wood or rubber; a ceramic material; glass; a yarn; a non-woven material (e.g. for diapers or the like, such as PP non-wovens); paper; leather or other textile (e.g. for clothing, for technical purposes, for canvas or the like, e.g. from cotton, wool, latex and/or synthetic fibres.

The substrate may be, for example, non-metal inorganic surfaces such as silica, silicon dioxide, titanium oxides, aluminum oxides, iron oxides, carbon, silicon, various silicates and sol-gels, masonry, and composite materials such as fiberglass and plastic lumber (a blend of polymers and wood shavings, wood flour or other wood particles).

The inorganic or organic substrate is, for example, a metal or metal alloy, a thermoplastic, elastomeric, inherently crosslinked or crosslinked polymer, a ceramic material or a glass.

The substrate may be a multi-layered article comprised of the same or different components in each layer. The surface coated, laminated and/or impregnated may be the exposed surface of an already applied coating or laminate.

The inorganic or organic substrate to be coated, laminated and/or impregnated can be in any solid form.

For example, polymer substrates may be plastics in the form of films, injection-molded articles, extruded workpieces, fibres, felts, non-woven or woven fabrics.

For example molded or extruded polymeric articles used in construction or the manufacture of durable goods such as siding, fascia and mailboxes can all benefit from the present method for stabilizer replenishment.

Plastics which would benefit from the uses or methods according to the invention include, but are not limited to, plastics used in construction or the manufacture of durable goods or machine parts, including outdoor furniture, boats, siding, roofing, glazing, protective films, decals, sealants, composites like plastic lumber and fiber reinforced composites, functional films including films used in displays as well as articles constructed from synthetic fibers such as awnings, fabrics such as used in canvas or sails and rubber articles such as outdoor matting and other uses cited in this disclosure. Exemplary of such plastics are polypropylene, polyethylene, PVC, POM, polysulfones, styrenics, polyamides, urethanes, polyesters, polycarbonate, acrylics, butadiene, thermoplastic polyolefins, ionomers, unsaturated polyesters and blends of polymer resins including ABS, SAN and PC/ABS.

The invention also provides a method of preventing biofouling of surfaces and/or materials, wherein a salt compound according to the invention (with a cation of the formula I) is incorporated into a coating formulation or film which is then applied to the surface of an article.

Examples of applications of the anti-fouling compositions of the instant invention are surface coatings, protective paints, impregnation compositions, other coatings and laminates applied to vulnerable surfaces, for example, the hulls of ships, surfaces of docks or the inside of pipes in circulating or pass-through water systems, walls exposed to rain water, walls of showers, roofs, gutters, pool areas, saunas, floors and walls exposed to damp environs such as basements or garages, the housing of tools and outdoor furniture.

For example, the anti-fouling compositions of the instant invention are found, among other places, on the surfaces and/or in the materials of: boat hulls, docks, buoys, drilling platforms, ballast water tanks, machines, machine parts, recreational, air conditioning systems, ion exchangers, process water systems, other industrial water systems, solar-powered units, heat exchangers, sump pumps, drainage systems, roofing, basements, walls, facades, greenhouses, sheds, storage areas, awnings, garden fencing, wood protection, tent roof material, fabrics, outdoor furniture, door mats, public conveniences, bathrooms, showers, swimming pools, saunas, jointing, sealing compounds, public conveyances, locker rooms, and the like.

Process water includes any process water stream which is used for heating or cooling purposes in closed or open circulating systems.

In order to be active against fungal and other microorganism and colonization by such organisms, a salt compound or an anti-fouling composition according to the invention can, alternatively or in addition to being used for a coating and/or for impregnating, also be admixed to materials or intermediate products used to form products or articles, e.g. to oligomer- and or pre-polymer mixtures or melts (e.g. for extrusion or molding) or components used to form articles from natural or especially synthetic materials, or e.g. to glue or other binding materials used to bind wood or other chips in the production of pressboard or imitation pressboard, to adhesives, cements or other mortar or concrete components, to mortars, to resins, to solutions or the like.

The antimicrobial and (especially with regard to colonization by organisms, especially fungi) anti-adhesive properties of the salt compounds of the present invention can be determined according to standard procedures, e.g. by the methods mentioned in the Examples. Such assays show a good to very good activity of the salt compounds according to the invention against fungal growth as well as for biofilm inhibition.

Preferred Embodiments of the Invention

The invention relates preferably to those embodiments where one or more of the more general definitions or symbols is or are replaced by a more specific definition given above or below.

Preferably, the invention relates to the antifungal use of a salt compound consisting of a cation of the formula I given above and one or more anions to form a neutral salt, as well as compositions containing an effective amount of such a salt, and to some novel salt compounds of this class.

Still more preferably, the invention relates to the use of a salt compound comprising or preferably consisting of at least one cation of the formula I, wherein
R1 is $C_1$-$C_{20}$-alkyl, phenyl, phenyl substituted by one to five moieties independently selected from the group consisting of $C_1$-$C_{10}$-alkyl, hydroxyl, $C_1$-$C_{10}$-alkoxy and $C_1$-$C_7$-alkanoyloxy; or phenyl-$C_1$-$C_{20}$-alkyl wherein phenyl is unsubstituted or substituted by one to five moieties independently selected from the group consisting of $C_1$-$C_{10}$-alkyl, hydroxyl, $C_1$-$C_{10}$-alkoxy and $C_1$-$C_7$-alkanoyloxy;
each of R2 and R3 is, independently of the other, $C_1$-$C_7$-alkyl,
each R4 is, independently of the other, hydroxy or $C_1$-$C_{30}$-alkanoyloxy;
$R_4'$ is hydrogen,
each R5 is $C_1$-$C_7$-alkyl, preferably methyl; and
n is 1 to about 30;
and one or more anions to form a neutral salt.

Yet more preferably the invention relates to the use of a salt compound comprising or preferably consisting of one or more cations of the formula I, wherein
R1 is $C_1$-$C_{20}$-alkyl;
each of R2 and R3 is, independently of the other, $C_1$-$C_7$-alkyl, preferably methyl;
each R4 is, independently of the other, hydroxy or $C_1$-$C_{10}$-alkanoyloxy;
$R_4'$ is hydrogen,
R5 is methyl; and
n is 1 to about 20;
and one or more anions to form a neutral salt.

A preferred embodiment of all embodiments of the invention described in the present disclosure relates to a salt according to the invention, wherein the cation of the formula I has a polydispersity of up to about 3.

Another preferred embodiment of the other embodiments of the inventions described in the present disclosure relates to a salt according to the invention, wherein the cation of the formula I has an average molecular weight of about 600 to about 3000.

The invention in a most preferred embodiment relates to a salt according to the invention as defined in one or more of the examples, as well as to a method of manufacture or use described in one or more of the examples.

The present invention also preferably relates to compositions comprising a cation of the formula I falling under the preferred embodiments of such cation, preferably with one or more other additives.

The invention relates also to compositions according to the invention comprising a preferred salt compound of the invention especially as described in the preceding preferred embodiments as antimicrobial agent and/or the use (or a method of using) according to the invention of a preferred salt compound of the invention especially as described in the preceding preferred embodiments or a composition comprising especially a preferred salt compound of the invention as described in the preceding preferred embodiments as antimicrobial agent as antimicrobial agent, comprising administering a composition or a salt compound according to the invention to a material or surface of a product or object. Where required, further steps, such as molding, curing or the like can follow. Administering may also take place by impregnation of an otherwise completed product, an intermediate product and/or a material.

EXAMPLES

The following Examples illustrate the invention without limiting its scope.

Example 1

The following compound of formula Ia according to the invention is prepared:

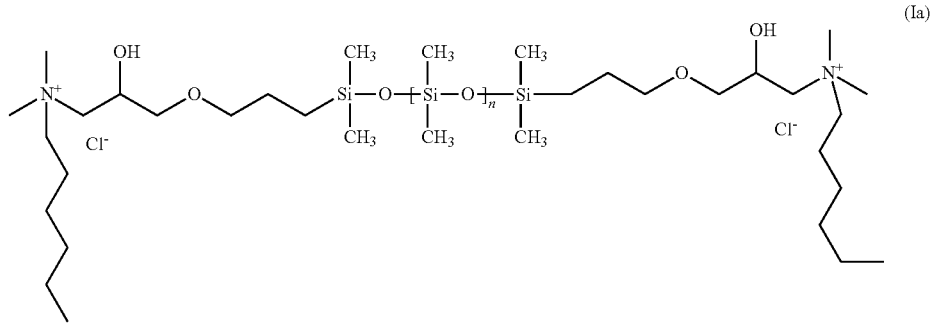

(Ia)

The mixture of 18.4 g (25 mmol) of the terminally epoxy-functionalized siloxane of the formula (A),

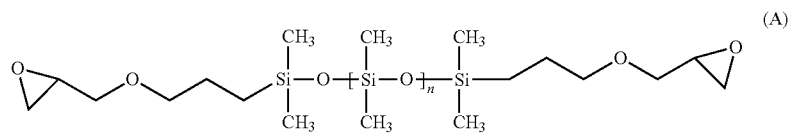

(A)

(wherein n=1-19; siloxane from GE Bayer Silicone GmbH & Co. KG, Leverkusen, Germany (GE was also called "General Electric" formerly), 8.4 g (50 mmol) dimethyl-(n-hexyl)- amine hydrochloride and a drop of triethylamine in 70 ml n-propanol is heated under reflux for 16 h. The solvent is evaporated under vacuum, the residue is taken up in 50 ml dichloromethane and the organic phase is washed one with 10 ml 1 n aqueous sodium hydroxide and once with 10 ml of water. After phase separation, the organic phase is obtained and evaporated to yield the title product obtained as yellow, viscous oil: 1H-NMR corresponds to expected structure (CDCL$_3$, δ 8 ppm]): 0 (m, 25H, SiCH$_3$), 0.40 (m, 2H, SiCH$_2$), 0.80 (m, 3H, CH$_3$), 1.25 (m, 6H, CH$_2$), 1.50 (m, 2H, CH$_2$), 1.65 (m, 2H, CH$_2$), 3.30-3.45 (m, 15H, N/OCH$_2$, NCH$_3$m CH), 4.35 (m, 1H, OH). LC/ESMS confirms molecular weight distribution m/z=622+n·37 (n=1-19).

Examples 2 to 6

The following compounds of the formula (Ia) to (If) are obtained analogously by reaction of the corresponding tert amine hydrochlorides with the siloxane of formula (A) given above (in each case, n=1-19):

| Example | Structure |
|---|---|
| 2 | 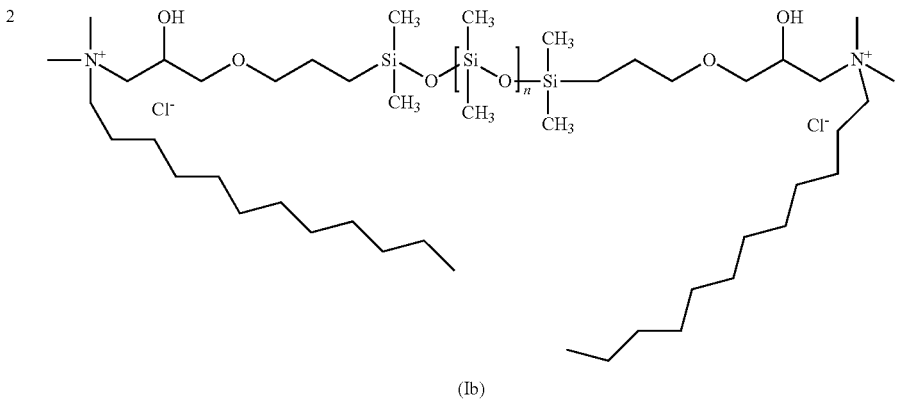 (Ib) |
| 3 | 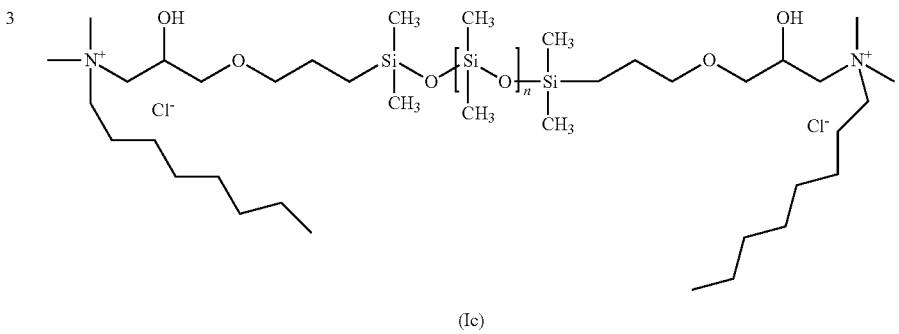 (Ic) |
| 4 | 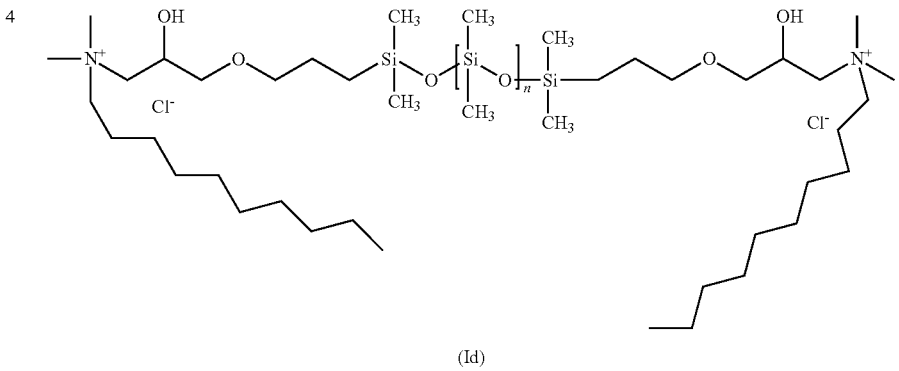 (Id) |

-continued

| Example | Structure |
|---|---|
| 5 | 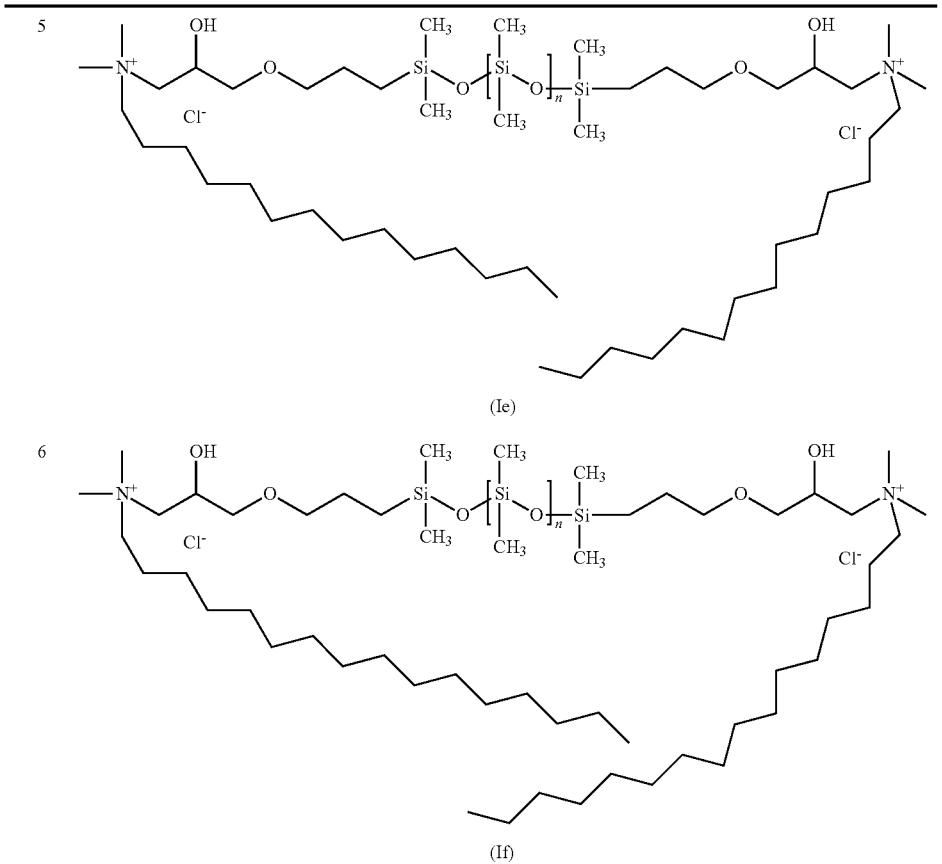 |

(Ie)

(If)

Example 7

Fungicidal Activity

Fungicidal activity is tested according to European Standard EN12175. A fungal spore suspension with a spore cell count of about $10^6$ cfu/ml is contacted with appropriate concentrations of the substances given in the table below and the residual spore cell count is determined after incubation times of 30 and 50 min at room temperature under continuous stirring. *Penicillium funiculosum* (DSM 1960), *Aspergillis niger* (DSM1957/ATCC 6275) and *Aureobasidium pullulans* (DSM2404) are tested as important mold strains. DSM refers to microorganisms obtainable under the number given at the DSMZ (Deutsche Sammlung von Mikroorganismen and Zellkulturen GmbH), Braunschweig, Germany. ATCC numbers refer to organisms obtainable from the American Type Culture Collection (see Ex. 7)

The results are given in the following table as a log reduction at each incubation time in comparison to a water control:

| Test conc. | | *P. funic* log reduction | | | *A. niger* log reduction | | | *P. funic* log reduction | | |
|---|---|---|---|---|---|---|---|---|---|---|
| (Example) | time | cfu/ml | 30 min | 1 h | cfu/ml | 30 min | 1 h | cfu/ml | 30 min | 1 h |
| Inoculum | | 4.60E+07 | | | 6.40E+07 | | | 1.0E+07 | | |
| H$_2$O | 30 min | 2.50E+06 | | | 2.70E+05 | | | 5.80E+05 | | |
| | 1 h | 2.90E+06 | | | 3.00E+05 | | | 6.70E+05 | | |
| 1% | 30 min | <10 | >4 | | 1.10E+04 | 1.4 | | <10 | >4 | |
| (Ex. 1) | 1 h | <10 | | >4 | 2.10E+03 | | 2.2 | <10 | | >4 |
| 1% | 30 min | <10 | >4 | | 4.10E+02 | 2.8 | | <10 | >4 | |
| (Ex. 2) | 1 h | ..<10 | | >4 | 1.00E+01 | | >4 | <10 | | >4 |
| 1% | 30 min | 3.00E+01 | >4 | | 2.00E+03 | 2.1 | | <10 | >4 | |
| (Ex. 6) | 1 h | <10 | | >4 | 1.20E+02 | | 3.4 | <10 | | >4 |

The tested examples show good to very good fungicidal activity.

Example 8

Biofilm Inhibition

The ability of the compounds of the invention for inhibiting the initial stages of biofilm formation is tested in a microplate based screening assay. Standard test specimen pins made of polycarbonate (of about 10 mm length, 2-3 mm diameter) are contacted with compound solutions in water or ethanol at a concentration of 0.5% for ½ hour for the compounds to form a film on the pin surface. The test pins are then dried at room temperature under laminar flow. The coated pins are contacted with a bacterial inoculum of *Staphylococcus aureus* at a cell count of $10^4$ to $10^5$ cfu/ml in a microplate and a biofilm is allowed to form on the plastic surface over 24 hours. Loosely attached cells are then rinsed off in a couple of rinsing steps with 0.9% saline, then the biofilm on the surface is removed by ultrasonic treatment. The eluted cells are transferred into new microplates in Caso broth (Sigma-Aldrich; tryptone soya broth, composition: 2.5 g/l dextrose, 2.5 g/l dipotassium phosphate, 3.0 g/l papaic digest of soya bean meal, 5.0 g sodium chloride, 17.0 g tryptone (vegetable)) and growth is allowed, monitored by measurement of the optical density at 620 nm over 24 hours.

The results are given as the OD 620 values at given time points over 24 hours incubation time in the following table:

| time [h] | average growth control | average Example 2 | average Example 3 | average Example 1 | average Example 4 | average Example 5 | average Example 6 |
| --- | --- | --- | --- | --- | --- | --- | --- |
| 0 | 0.006 | 0.002 | 0.001 | 0.001 | 0.001 | 0.001 | 0.001 |
| 0.5 | 0.005 | 0.000 | −0.001 | −0.001 | −0.001 | −0.001 | 0.000 |
| 1 | 0.006 | 0.000 | −0.001 | −0.001 | −0.001 | −0.001 | 0.000 |
| 1.5 | 0.009 | 0.000 | −0.001 | −0.001 | −0.001 | −0.001 | 0.000 |
| 2 | 0.017 | 0.001 | 0.001 | 0.000 | 0.000 | 0.000 | 0.000 |
| 2.5 | 0.031 | 0.001 | −0.001 | −0.002 | −0.001 | −0.001 | −0.001 |
| 3 | 0.064 | 0.004 | 0.000 | −0.001 | 0.000 | 0.000 | 0.000 |
| 3.5 | 0.115 | 0.007 | 0.000 | −0.001 | −0.001 | −0.001 | 0.000 |
| 4 | 0.185 | 0.016 | 0.001 | −0.001 | 0.000 | 0.000 | 0.000 |
| 4.5 | 0.267 | 0.029 | 0.001 | −0.001 | 0.000 | 0.000 | 0.000 |
| 5 | 0.329 | 0.048 | 0.001 | −0.001 | −0.001 | −0.001 | 0.000 |
| 5.5 | 0.389 | 0.072 | 0.000 | −0.002 | −0.002 | −0.002 | −0.001 |
| 6 | 0.419 | 0.103 | 0.000 | −0.002 | −0.002 | −0.001 | −0.001 |
| 6.5 | 0.454 | 0.141 | 0.000 | −0.002 | −0.002 | −0.002 | −0.001 |
| 7 | 0.471 | 0.180 | −0.001 | −0.003 | −0.003 | −0.002 | −0.002 |
| 7.5 | 0.483 | 0.223 | 0.001 | −0.002 | −0.001 | −0.001 | −0.001 |
| 8 | 0.488 | 0.263 | 0.000 | −0.002 | −0.002 | −0.002 | −0.001 |
| 8.5 | 0.492 | 0.299 | 0.000 | −0.002 | −0.002 | −0.002 | −0.002 |
| 9 | 0.494 | 0.325 | 0.000 | −0.002 | −0.002 | −0.002 | −0.001 |
| 9.5 | 0.497 | 0.346 | 0.000 | −0.002 | −0.002 | −0.002 | −0.001 |
| 10 | 0.497 | 0.360 | 0.001 | −0.002 | −0.002 | −0.001 | −0.001 |
| 10.5 | 0.497 | 0.369 | 0.001 | −0.002 | −0.002 | −0.002 | −0.001 |
| 11 | 0.495 | 0.376 | 0.001 | −0.002 | −0.002 | −0.001 | −0.001 |
| 11.5 | 0.493 | 0.380 | 0.000 | −0.003 | −0.003 | −0.002 | −0.002 |
| 12 | 0.492 | 0.384 | 0.001 | −0.002 | −0.002 | −0.001 | −0.001 |
| 12.5 | 0.491 | 0.385 | 0.000 | −0.002 | −0.002 | −0.002 | −0.001 |
| 13 | 0.489 | 0.386 | 0.000 | −0.003 | −0.003 | −0.002 | −0.002 |
| 13.5 | 0.489 | 0.386 | 0.000 | −0.002 | −0.003 | −0.002 | −0.002 |
| 14 | 0.486 | 0.386 | 0.000 | −0.003 | −0.003 | −0.003 | −0.002 |
| 14.5 | 0.484 | 0.387 | 0.000 | −0.002 | −0.002 | −0.002 | −0.002 |
| 15 | 0.482 | 0.387 | 0.000 | −0.002 | −0.002 | −0.002 | −0.002 |
| 15.5 | 0.481 | 0.386 | 0.000 | −0.003 | −0.003 | −0.003 | −0.002 |
| 16 | 0.478 | 0.385 | 0.000 | −0.003 | −0.003 | −0.003 | −0.002 |
| 16.5 | 0.476 | 0.385 | 0.000 | −0.002 | −0.002 | −0.002 | −0.002 |
| 17 | 0.473 | 0.384 | 0.000 | −0.003 | −0.003 | −0.003 | −0.002 |
| 17.5 | 0.470 | 0.384 | −0.001 | −0.003 | −0.003 | −0.003 | −0.003 |
| 18 | 0.468 | 0.385 | 0.000 | −0.002 | −0.002 | −0.002 | −0.002 |
| 18.5 | 0.463 | 0.385 | 0.000 | −0.003 | −0.003 | −0.003 | −0.003 |
| 19 | 0.460 | 0.386 | 0.000 | −0.003 | −0.003 | −0.003 | −0.002 |
| 19.5 | 0.455 | 0.386 | 0.000 | −0.003 | −0.003 | −0.003 | −0.003 |
| 20 | 0.451 | 0.387 | 0.000 | −0.003 | −0.003 | −0.002 | −0.002 |
| 20.5 | 0.446 | 0.386 | 0.000 | −0.003 | −0.003 | −0.003 | −0.002 |
| 21 | 0.442 | 0.386 | 0.000 | −0.003 | −0.003 | −0.003 | −0.002 |
| 21.5 | 0.436 | 0.387 | 0.000 | −0.003 | −0.003 | −0.003 | −0.002 |
| 22 | 0.429 | 0.389 | 0.000 | −0.003 | −0.003 | −0.003 | −0.002 |
| 22.5 | 0.423 | 0.390 | 0.000 | −0.003 | −0.003 | −0.003 | −0.002 |
| 23 | 0.417 | 0.390 | −0.001 | −0.004 | −0.003 | −0.003 | −0.003 |
| 23.5 | 0.410 | 0.391 | −0.001 | −0.004 | −0.004 | −0.003 | −0.003 |
| 24 | 0.404 | 0.392 | 0.000 | −0.003 | −0.003 | −0.003 | −0.002 |

No growth as compared to a growth control (average growth without presence of inhibitor), that is, full initial biofilm inhibition, can be observed with the compounds from Examples 1, 3, 4, 5 and 6, respectively.

Example 9

Efficacy in Flexible PVC, LDPE and Latex-Based Paints

A solution of the salt compound of example 1 is a solvent (tetrahydrofurane and/or acetone) is prepared with a concentration of 1% of the salt compound of example 1. This solution is soicated for 1 min to ensure complete dissolution of the test salt compound. Then, the material shown in the below table (10×10 cm) is dipped into the solution (100 ml) and left under sonication for 1 min. The material is taken out of the solution and dried on air at room temperature for some hours. This coated sheet is then used for microbiological testing as follows:

The efficacy of the salt compound of Example 1 is tested according to a modified AATCC-100 standard for assessing antibacterial activity on textiles. Overnight cultures of two test bacteria are contacted with the treated material by pipetting a diluted suspension onto the surface of the material. The material is then incubated for 24 h at 37° C., and then the cell count is determined by elution of the materials into a neutralizing medium, dilution series and plate counting technique. *Staphylococcus aureus* is used as the gram+ and *Escherichia coli* as the gram-organism, and *Aspergillus pullulans* and *Aspergillus niger* as fungal strains.

The blanks show full growth of both organisms over the incubation time, while the material treated with the compound of Example 1 (formula (Ia)) as compiled in the below table does not show any growth (active: inoculum cell count reduced to below detection limit).

| Material | Concentration of salt compound example 1 | Test organisms | Result |
|---|---|---|---|
| Flexible PVC | 0.2 & 0.5% | S. aureus, A. pullulans | 0.2% active 0.5% active |
| Water-based latex paint | 0.5 & 2% | S. aureus, A. niger, A. pullulans | 0.5% +/− active 2% active 2% active |

The invention claimed is:
1. A method for the fungicidal protection of a material, intermediate or product in need thereof said method comprises adding an effective amount of a salt compound or a composition comprising a cation selected from the group consisting of

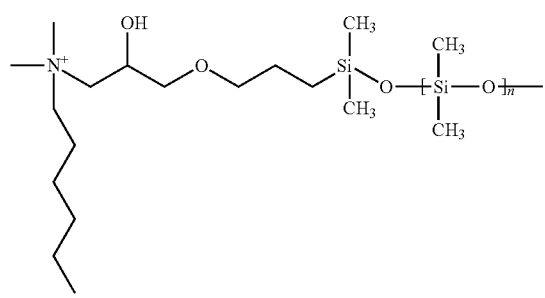

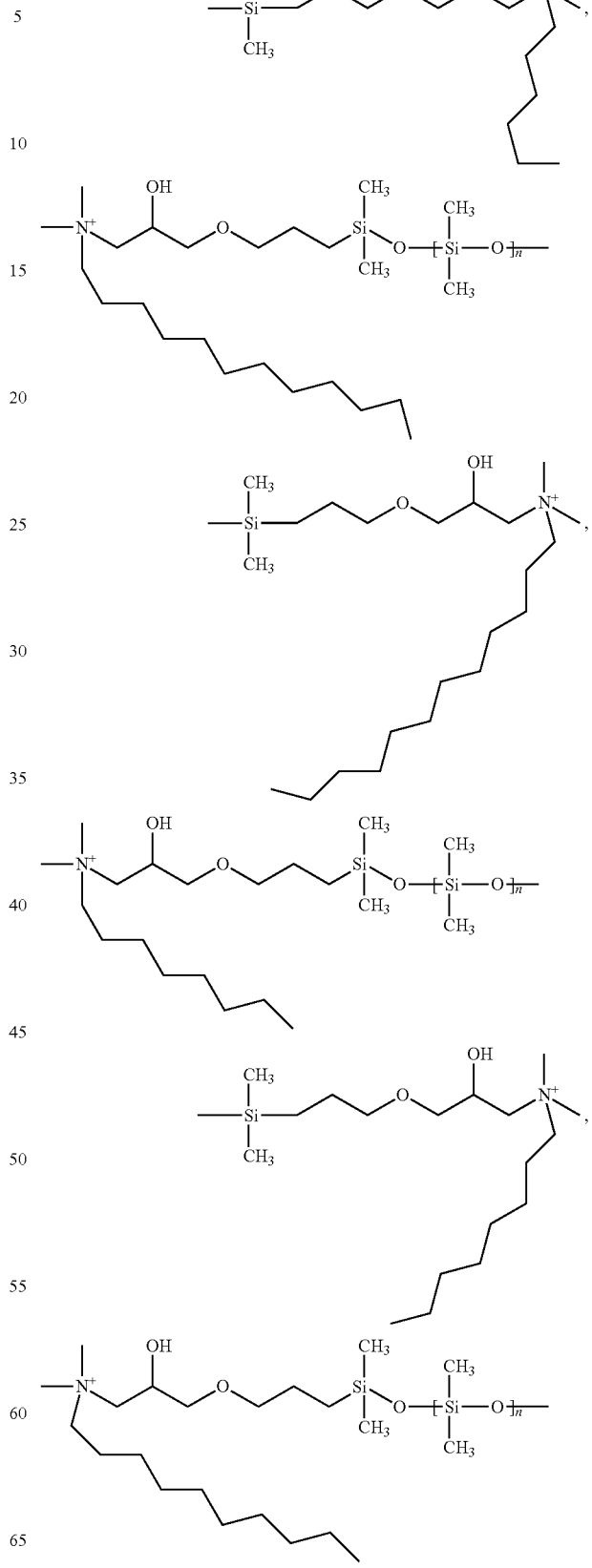

-continued

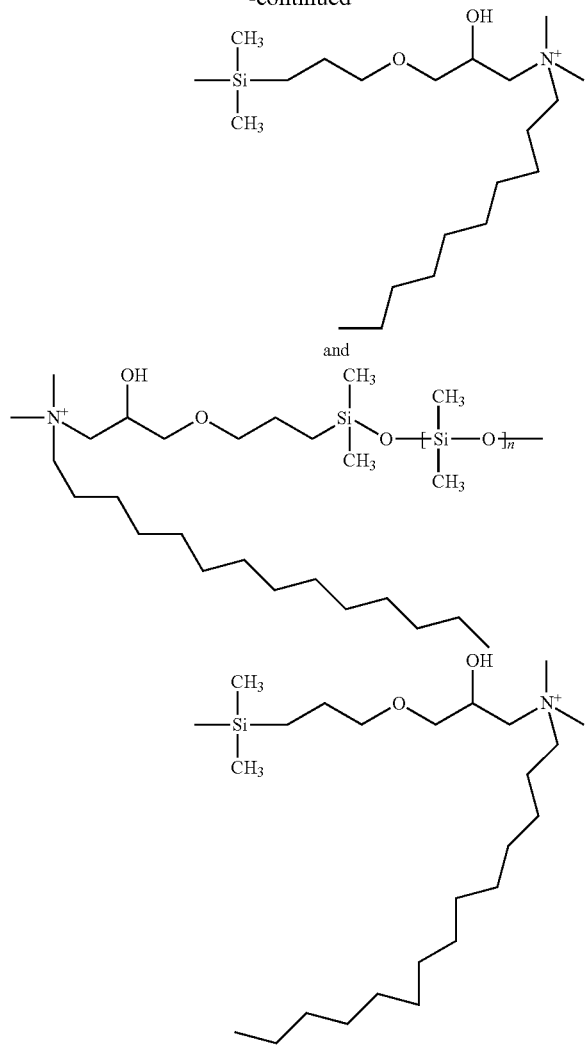

wherein n is a number from 1 to 19

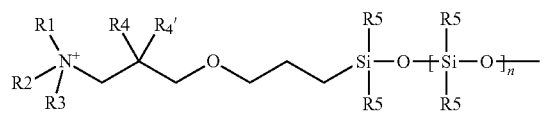 (I)

-continued

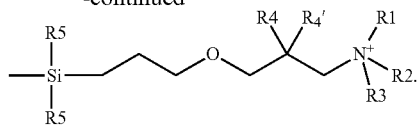

2. A method according to claim 1 wherein one or more anions are mono- or discharged anions and per cation of the formula p anions of the formula (IA)

$$Y^{(3-p)-} \quad \text{(IA)}$$

are present with more than one type of Y wherein
Y is an anion molecule with the integer number of negative charges determined by (3-p) and
p is 1 or 2.

3. A method according to claim 1 wherein one or more anions are selected from the group consisting of chloride, iodide, bromide, fluoride, sulfate, hydrogensulfate, nitrate, hydrogenphosphate, phosphate, borate, tetrafluoroborate, acetate, citrate, p-toluenesulfate, methansulfonate, methyloxysulfonate, trifluoromethansulfonate, nonafluorobutanesulfonate, 2,2,2-trifluoroethanesulfonate and fluorosulfonate.

4. A method according to claim 1 where the cation of formula I has a polydispersity of up to about 3.

5. A method according to claim 1 wherein the cation of formula I has an average molecular weight of about 600 to about 3000.

6. A method for the inhibition of a biofilm on a surface of a material said method comprises adding to said surface an effective amount of a salt compound comprising a cation according to claim 1.

7. A method according to claim 2 wherein one or more anions are mono- or discharged anions and per cation of the formula p anions of the formula (IA)

$$Y^{(3-p)-} \quad \text{(IA)}$$

are present with one type of Y wherein
Y is an anion molecule with the integer number of negative charges determined by (3-p) and
p is 1 or 2.

8. A method according to claim 3 wherein one or more anions are selected from the group consisting of chloride, iodide, bromide, fluoride, tetrafluoroborate, hydrogensulfate and methyloxysulfonate.

9. The method according to claim 1, wherein n is 5.

10. The method according to claim 1, wherein the fungicidal protection is characterized by a log reduction on the residual spore cell count tested according to European Standard EN12175 in comparison to a water control.

* * * * *